(12) United States Patent
Chen

(10) Patent No.: US 6,737,279 B1
(45) Date of Patent: May 18, 2004

(54) TUNING THE PROPERTIES OF CONJUGATED POLYELECTROLYTES AND APPLICATION IN A BIOSENSOR PLATFORM

(75) Inventor: Liaohai Chen, Los Alamos, NM (US)

(73) Assignee: The Regents of the University of California, Los Alamos, CA (US)

( * ) Notice: Subject to any disclaimer, the term of this patent is extended or adjusted under 35 U.S.C. 154(b) by 0 days.

(21) Appl. No.: 09/820,402

(22) Filed: Mar. 28, 2001

(51) Int. Cl.⁷ ................ G01N 33/533; C07K 17/08; C12N 11/08
(52) U.S. Cl. ............... 436/546; 435/6; 435/188; 436/531; 436/532; 436/533; 530/391.5
(58) Field of Search ................ 436/531, 532, 436/533, 546; 530/391.5; 435/6, 188

(56) References Cited

U.S. PATENT DOCUMENTS

| | | | | |
|---|---|---|---|---|
| 5,166,320 A | * | 11/1992 | Wu et al. | |
| 5,670,381 A | * | 9/1997 | Jou et al. | |
| 5,866,322 A | * | 2/1999 | Jou et al. | |
| 6,251,866 B1 | * | 6/2001 | Prakash et al. | |
| 6,312,727 B1 | * | 11/2001 | Schacht et al. | |

FOREIGN PATENT DOCUMENTS

| | | | |
|---|---|---|---|
| WO | WO0066790 | | 11/2000 |
| WO | 00/66790 | * | 11/2000 |

OTHER PUBLICATIONS

J. Xia et al. J. Phys. Chem., vol. 97, pp. 4528–4534 (1993).*
L. Chen et al., "Surfactant–Induced Modification of Quenching of Conjugated Polymer Fluorescence by Electron Acceptors: Applications for Chemical Sensing", Chem. Phys. Lett., v. 330(#1–2) pp. 27–33, Nov. 3, 2000.

L. Chen et al., "Superquencing Behavior Between a Conjugated Polymer and Molecular Quenchers and Its Application in Biological/Chemical Sensors", Proc. SPIE–Int. Soc. Opt. Eng. (1999), v. 3858, 32–39.

J. Y. Gao et al., "Capillary Electrophoresis and Dynamic Light Scattering Studies of Structure and Binding Characteristics of Protein–Polyelectrolyte Complexes", J. Phys Chem. B, 1998, v. 102, pp. 5529–5535.

* cited by examiner

*Primary Examiner*—Mary E. Ceperley
(74) *Attorney, Agent, or Firm*—Bruce H. Cottrell

(57) ABSTRACT

The present invention provides a method of detecting a biological agent including contacting a sample with a sensor including a polymer system capable of having an alterable measurable property from the group of luminescence, anisotropy, redox potential and uv/vis absorption, the polymer system including an ionic conjugated polymer and an electronically inert polyelectrolyte having a biological agent recognition element bound thereto, the electronically inert polyelectrolyte adapted for undergoing a conformational structural change upon exposure to a biological agent having affinity for binding to the recognition element bound to the electronically inert polyelectrolyte, and, detecting the detectable change in the alterable measurable property. A chemical moiety being the reaction product of (i) a polyelectrolyte monomer and (ii) a biological agent recognition element-substituted polyelectrolyte monomer is also provided.

4 Claims, 3 Drawing Sheets

TUNING THE PROPERTIES OF CONJUGATED POLYELECTROLYTES AND APPLICATION IN A BIOSENSOR PLATFORM

STATEMENT REGARDING FEDERAL RIGHTS

This invention was made with government support under Contract No. W-7405-ENG-36 awarded by the U.S. Department of Energy. The government has certain rights in the invention.

FIELD OF THE INVENTION

The present invention relates generally to highly sensitive biological sensors, to a method for the detection of biological agents using such sensors, to a polymer system for use in such sensors, and to chemical moieties for inclusion in such polymer systems.

BACKGROUND OF THE INVENTION

The desirable properties of conjugated polymers depend on their intense fluorescence and highly delocalized photophysical properties. These properties are important for a variety of applications ranging from LED to a recently demonstrated biosensing application (WO 00/66790) to manipulate the fluorescence quantum efficiency (QE) and control both the wavelength and excited state decay channels present in the conjugated polymer. In previous studies it was discovered that the fluorescence QE of an ionic conjugated polymer can be increased through interacting with small amount of certain detergents (Chem. Phys. Lett., v. 330(#1–2) pp.27–33, Nov. 3, 2000). It was believed that the surfactant can inhibit the folding of the polymer chains, reduce the conformational disorder and thus increase the QE.

In WO 00/66790, a conjugated polymer base biosensor was developed, in which the signal transduction came from the reversal of quenched polymer fluorescence by a quencher-ligand diad. While that biosensor system is quite successful in detecting various of toxins and viruses, one drawback is the non-specific interactions between the ionic conjugated polymer and proteins, which can also cause a change in the fluorescence of the conjugated polymer. The interactions of polyelectrolytes with proteins are well known processes, which actually have drawn lots of attention in the literature due to importance of such interactions in natural biological systems as well as biotechnological applications.

SUMMARY OF THE INVENTION

In accordance with the purposes of the present invention, as embodied and broadly described herein, the present invention includes a chemical moiety comprising the reaction product of (i) a polyelectrolyte monomer and (ii) a biological agent recognition element-substituted polyelectrolyte monomer.

The present invention also includes a polymer system including an ionic conjugated polymer, and, an electronically inert polyelectrolyte having a biological agent recognition element bound thereto.

The present invention also includes method of detecting a biological agent including contacting a sample with a sensor including a polymer system capable of having an alterable measurable property selected from the group consisting of luminescence, anisotropy, redox potential and uv/vis absorption, said polymer system including an ionic conjugated polymer and an electronically inert polyelectrolyte having a biological agent recognition element bound thereto, said electronically inert polyelectrolyte adapted for undergoing a conformational structural change upon exposure to a biological agent having affinity for binding to said recognition element bound to said electronically inert polyelectrolyte, and, detecting said detectable change in said alterable measurable property.

The present invention also includes sensor including a polymer system capable of having an alterable measurable property selected from the group consisting of luminescence, anisotropy, redox potential and uv/vis absorption, said polymer system including an ionic conjugated polymer and an electronically inert polyelectrolyte having a biological agent recognition element bound thereto, said electronically inert polyelectrolyte adapted for undergoing a conformational structural change upon exposure to a biological agent having affinity for binding to said recognition element bound to said electronically inert polyelectrolyte whereby a detectable change in said alterable measurable property can occur, and, a means of detecting said detectable change in said alterable measurable property.

The present invention also includes a process of tuning the properties of an ionic conjugated polymer including admixing an ionic conjugated polymer with an electronically inert polyelectrolyte comprising the reaction product of (i) a polyelectrolyte monomer and (ii) a biological, agent recognition element-substituted polyelectrolyte monomer.

The present invention also includes a kit for the detection of biological agents including a fluorescent polymer, and, an electronically inert polyelectrolyte having a biological agent recognition element bound thereto.

DETAILED DESCRIPTION

Another way has now been found to dramatically increase the quantum efficiency (QE) of the ionic conjugated polymer through complexing with a. template polymer. More importantly, the unique photophysic properties of the complex formed between the conjugated and template polymers have been utilized to construct a novel sensitive biosensor platform.

Figure 2:
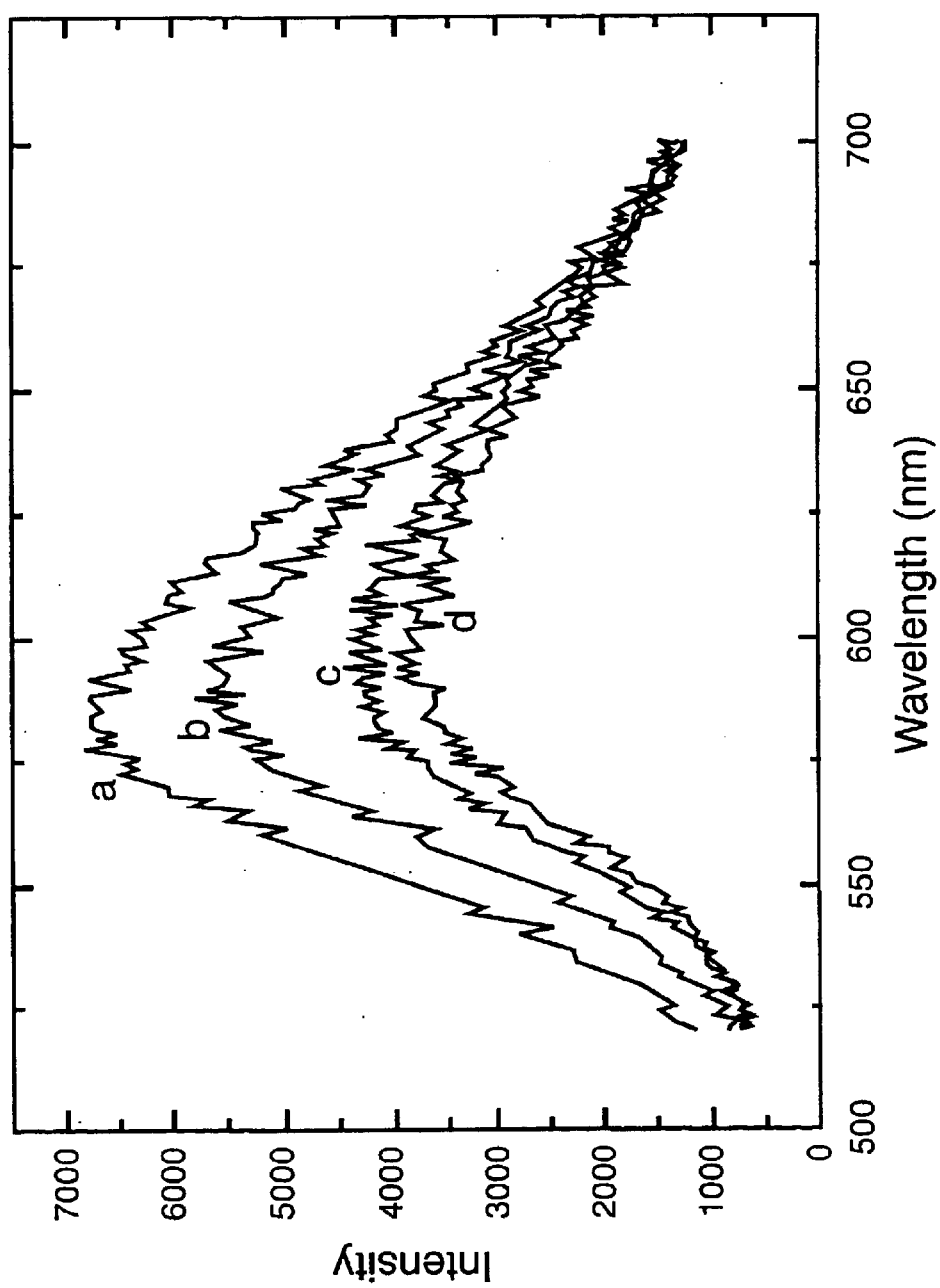
FIG. 2 shows a graph of the fluorescence spectra of a MPS-PPV complex in the presence of varying concentrations of avidin.

Ionic conjugated polymers, newly emerged polymer materials, are different from conventional polyelectrolytes by consisting of both polyions and electronically conjugated backbones. It is commonly accepted that the polyelectrolyte has expanded rod-like conformation in aqueous solution because of the electrostatic repulsion of the uncompensated charges on the polymer, and the polymer chains can be homogeneously distributed through the solution. For the conjugated polyelectrolyte, the situation is getting more complicated due to the additional interactions between both intro and inter polymer backbones (such as $\pi$-$\pi$ interactions). Even though there have been no systematic studies for the conformation of the conjugated polyelectrolyte, the fact that addition of surfactant to the conjugated polyelectrolyte solution can stretch the polymer backbone and make it more ordered implies that the conjugated polyelectrolyte may coil in the aqueous solution. Thus by mixing these two polymers together, the rod-like conventional polyelectrolyte may provide a linear template for the ionic conjugated polymer. Under the influence of the linear template, the conjugate polymer backbone may become more ordered, and consequently the fluorescence QE could be increased;

Exemplary of a suitable ionic conjugated polymer is a poly(phenylene vinylene) derivative, 2-methoxy-5-propyloxysulfonato phenylene vinylene (MPS-PPV). The synthesis and photophysics of MPS-PPV have been previously described by Chen et al., Proc.SPIE-Int. Soc. Opt. Eng. (1999), 3858, 32–39. The disordered (coiled) conformation of MPS-PPV in aqueous solution is characterized by its site-selective fluorescence and broad structure-less emission spectra. By adding electronically inert polyelectrolytes to the MPS-PPV solution (or adding the MPS-PPV solution to electronically inert polyelectrolytes), the fluorescence QE of the conjugated polymer is dramatically increased. Exemplary of suitable polyelectrolytes are included cationic polymers such as poly (diallydimethylammonium chloride) (PDDA), polyethylenimine (PEI) and the like, neutral polymers such as poly (ethylene glycol) (PEG) and the like, and anionic polymers such as poly(acrylic acid) (PAA), poly (sodium 4-styrenesulfonate) (PSS) and the like. While all of the above polyelectrolytes can increase the QE at certain levels, neutral and anionic polymers are the preferred polyelectrolytes as they have been found to have the largest effect. For example, as shown in FIG. 2, upon adding PAA (up to 25 mM) (all polymer concentrations refer in repeating units) to an aqueous MPS-PPV solution ($1\times10^{-5}$ M), the fluorescence of intensity is increased approximately 10-fold. The emission spectra not only are wavelength independent, but also show sharper structure.

While not wishing to be bound by the present explanation, it is believed that the above observation clearly indicates an ordered structure for the conjugate polymer in the presence of template polymers. Given the conformation of template polymers in the solution as discussed above, i is reasonable to assume that the rod-like polyelectrolyte provides a linear matrix in the aqueous solution and induces the conformational change of the conjugated polymer. The slight increase of viscosity might also contribute to the increase of QE, the fact that the amplification effect saturates at a template polymer concentration of 25 mM suggest that it plays a minor role. Since properties of a conjugated polymer are sensitive to its conformational change, the linear geometry of the template polymer will extend the conjugated polymer chains, reduce the conformational disorder, and increase the QE. The advantage of using template polymers instead of surfactants to manipulate the polymer fluorescence is that the resulting material is much easier to process. Especially when using a neutral template the charges on the conjugated polymer backbone are still available for further complexation. For example, it was found that methyl viologen can still quench the polymer fluorescence with a quenching constant of $2\times10^7$ $M^{-1}$ in the presence of PEG as the template.

For a cationic polyelectrolyte template such as PDDA, the situation is quite different. Due to the interaction of oppositely charged polyions, the resulting structure of interpolyelectrolyte complex is far more complicated. As a result, when the concentration of PDDA is higher (0.5 mM) than that for MPS-PPV ($1\times10^{-5}$ M), it can only double the QE; on the other hand, when its concentration is closer to the concentration of MPS-PPV, it actually quenches the MPS-PPV fluorescence. The maximum quenching happens when the ratio of PDDA MPS-PPV PPV is 3:2. Interestingly, this result is quite consistent with related literature values. For example, Pogoina et al., Macromolecules, 1997, v. 30, pp. 4897–4904, have studied the interactions of cationic poly (vinylpyridinium) and anionic poly(sodium styrenesulfonate), and found that the strongest interpolyelectrolyte interaction occurs with 60% of the polycation component and 40% of the polyanion component.

The formed complexes of the present invention are quite stable in the aqueous solution and its fluorescence intensity does not change even for weeks. It was also found that such complexes are quite stable to the presence of high ion strength or proteins. For example, once a complex is formed, the photophysical properties of the complex (such as absorption or fluorescence) did not change at all when certain amount of proteins (up to 0.5 mg/ml) such as avidin or bovine serum albumin (BSA) is added to the solution. This is in sharp contrast to the addition of such proteins to the MPS-PPV solution alone, which results in the increase of polymer fluorescence. It has also been reported by Gao et al., J. Phys. Chem. B, 1998, v. 102, pp. 529–5535 that a strong complex can be formed between BSA and PDDA, which is confirmed by capillary electrophoresis and dynamic light scattering experiment. Thus, the interpolyelectrolyte reaction between MPS-PPV and PDDA provides an effective method to eliminate nonspecific binding processes between the polyelectrolyte and the protein.

Avoidance of non-specific binding in order to apply the ionic conjugated polymer to a biosensor platform was a key concern in the development of the present invention. It was found that non-specific binding was not a specific problem for the present conjugated polymer based biosensor, whereas it is the major challenge for many current protein detection assays due to the sticky nature of proteins.

The discovery that the photophysics properties of the complex formed between the conjugated and template polymers are very robust, i.e., the physical properties are largely unaffected by high ionic strengths in the solution or by the presence of biological molecules, provided a unique opportunity in construction of the present biosensor platform. Since the fluorescence of conjugated polymers is strongly dependent upon its conformation, and the conjugated and template polymers are closely associated with each other in the complex, any changes of the template polymer will induce the conformation change for the conjugated polymer, and consequently can be characterized by its property change. Thus, the conjugated polymer can function as a sensitive probe to signal the geometric change of template polymers providing that such change is induced by a specific bio-recognition event.

The sensors of the present invention may be used to detect either biological agents or chemical agents. However, it is expected that such sensors may have greater advantages in the detection of selected biological agents wherein there is a matching pair of a biological recognition element and a biological agent having a high affinity (a high K) that trigger the binding and subsequent signal event. For example, the detected biological agent can be from among the group of proteins, amino acids, oligonucleotides, hormones, vitamins, viruses, bacteria, cells, microorganisms, antibody fragments, and toxins. Exemplary of such agents are included the following: influenza, parainfluenza, hepatitis, streptococcus, staphylococcus, HIV, anthrax, cholera, and the like.

The recognition element of the intermediate combination must be capable of recognizing and binding to a selected chemical or biological species, preferably a biological species. For example, the recognition element can be from among chemical ligands, antibodies, polynucleotides, antigens, polypeptides, and polysaccharides. Combinations of pairs that are categorizable as recognition element-chemical or biological species pairs are well know to those skilled in the art. For example, immunoassays are based on antigen-antibody affinity interactions. Similarly recognized pairs include: hormone-hormone receptor pairs; polynucleotide strand-complementary polynucleotide strand pairs; enzyme-enzyme cofactor or inhibitor pairs; avidin-biotin; protein A-immunoglobulin; and, lectins-specific carbohydrates.

Another recognized pair is cholera toxin (CT) and ganglioside GM1. Gangliosides are a class of molecules which are glycolipids. Different gangliosides have been identified as prominent cell surface constituents of various cells. Gangliosides are known as mono-, di-, tri or polysialogangliosides, depending upon the degree of glycosylation with sialic acid residues. Abbreviations employed to identify these molecules include "GM1", "GD3", "GT1", etc., with the "G" standing for ganglioside, "M", "D" or "T", etc. referring to the number of sialic acid residues, and the number or number plus letter (e.g., "GT1a"), referring to the binding pattern observed for the molecule. Cholera toxin is an $AB_5$ hexameric protein with five identical B subunits which define the binding region and one A subunit responsible for catalysis. Toxicity of the cholera toxin is initiated by the recognition and binding of B sub-units to a pentasaccharide moiety of GM1 in the cell surface followed by a mechanism involved in the entry of an A sub-unit through the membrane into the cell.

The present invention further includes a kit for the detection of biological agents. Such a kit can generally include a fluorescent polymer such as described previously and a chemical moiety as described previously.

Figure 3:
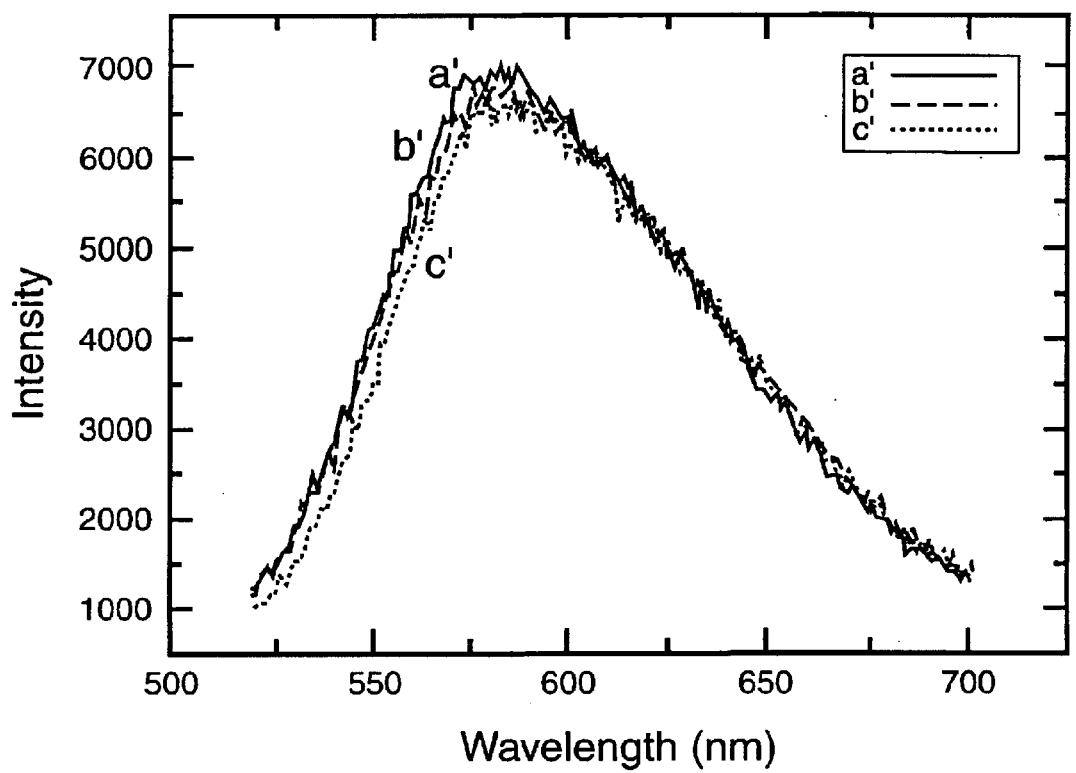
FIG. 3 shows a graph of the fluorescence spectra of a second MPS-PPV complex in the presence of varying concentrations of avidin.

Accordingly, as shown in scheme 1 below, a diallylammonium derivative linked with biotin molecule (2) was synthesized, and that product (2) was polymerized with the monomer of PDDA (1) to yield a biotin modified template polymer (3). That product (3) formed a stable complex with MPS-PPV in an aqueous solution. Due to the specific binding between the avidin protein and biotin receptor linked to the template backbone, the avidin protein causes a conformational change to the template polymer, and consequently triggers the property change of the conjugate polymer. Indeed, as shown in FIG. 3, the addition of nanomolar concentrations of avidin protein to a MPS-PPV-(3) complex induced the decrease of MPS-PPV fluorescence; while the controlled experiment of the addition of the same amount of avidin to MPS-PPV-PDDA (4) complex solution resulted in no fluorescence change. It is also demonstrated that the presence of albumin protein (0.1 mg/ml) does not affect the sensor performance at all. This system is successful in detection of trace amounts of avidin protein in the solution. Thus, it is realized that such a sensor array can be rationally generalized by synthesizing template polymers with appropriate bio-recognition components attached.

Scheme 1

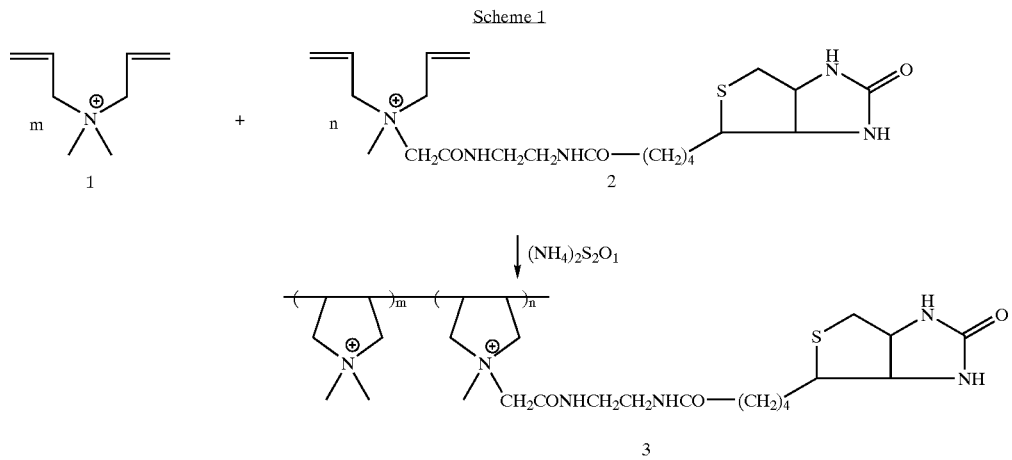

The fluorescent quantum efficiency of an ionic conjugated polymer can be finely tuned by complexation with a template polyelectrolyte. The properties of the resulting complex are robust towards the high ionic strength and the presence of biological molecules. By tethering a bio-ligand to the template polymer, the conjugated polymer can function as the signal transducer to sense the corresponding biomolecules with high sensitivity. The signal transduction is achieved by a property change in the conjugate polymer induced by the interaction of the biomolecule with the template polymer. The inherent advantage of this biosensor is that it can effectively prevent the non-specific binding while retaining a high sensitivity. Other property changes of the conjugated polymer such as anisotropy and redox may also be used as signal transductions.

The present invention is more particularly described in the following examples, which are intended as illustrative only, since numerous modifications and variations will be apparent to those skilled in the art.

EXAMPLE 1

Figure 1:
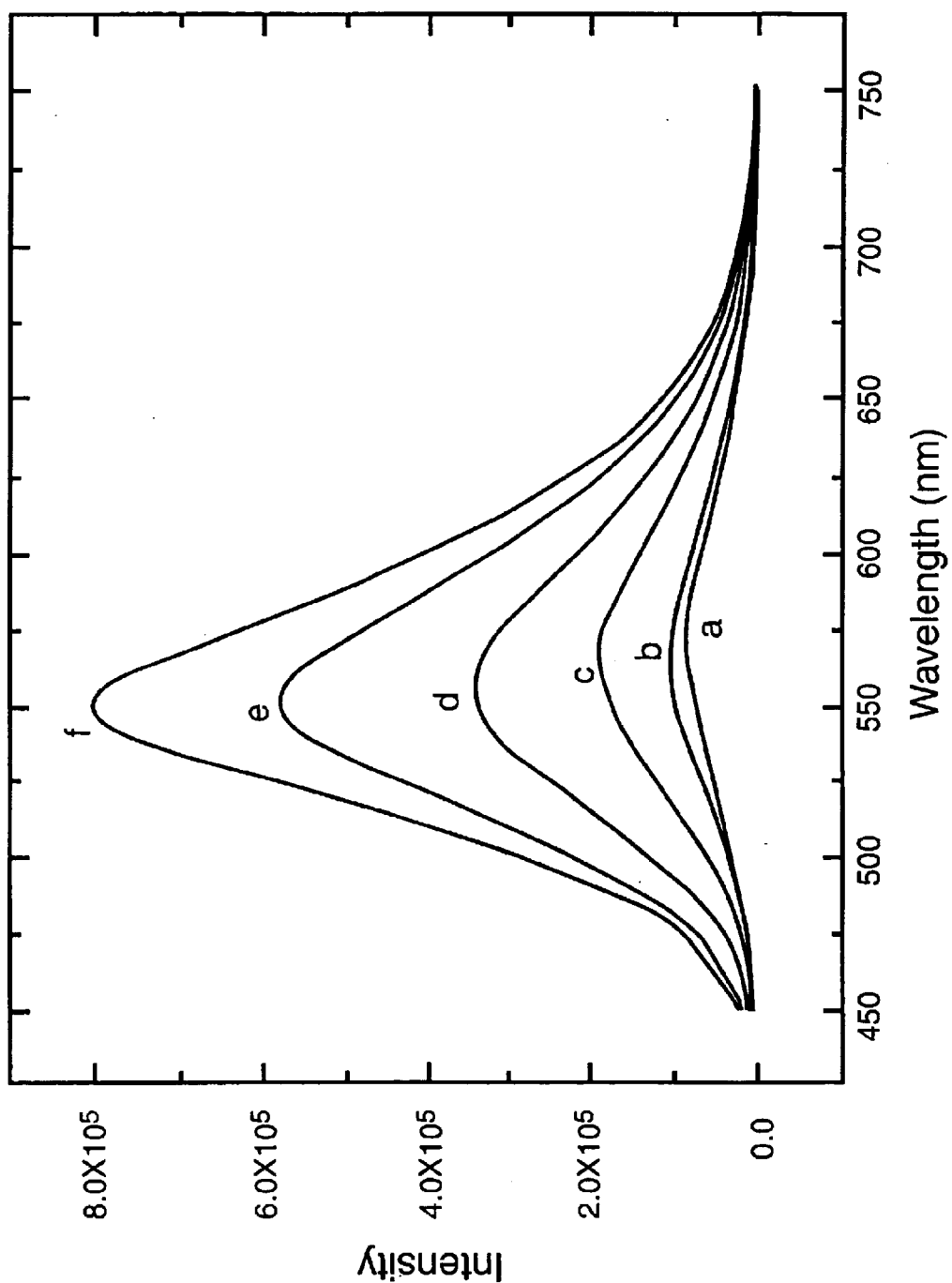
FIG. 1 shows a graph of the fluorescence spectra of MPS-PPV at a concentration of $1 \times 10^{-5}$ M in the presence of varying concentrations of poly(acrylic acid) (PAA).

Demonstration that the fluorescence quantum efficiency of MPS-PPV solution can be increased by adding a variety of polylelectrolytes, e.g., poly (acrylic acid) (PAA), was as follows. For example, as shown in FIG. 1, upon adding PAA (up to 25 mM) (all polymer concentrations refer in repeating units) to an aqueous MPS-PPV lo solution ($1 \times 10^{-5}$ M), the fluorescence of intensity was increased approximately 10-fold. The fluorescence spectra were recorded on a PTI Quantamaster Spectrofluorometer with excitation at 500 nm. The concentration of MPS-PPV was $1 \times 10^{-5}$ M, and the concentrations of added PAA were: a: 0 mM; b: 0.2 mM; c:

0.8 mM; d: 2.2 mM; e: 11.2 mM; f: 22.4 mM. Similar results can also obtain when using a neutral polymer such as PEG.

EXAMPLE 2

Detection of avidin protein using MPS-PPV and template polymer 3 complex was demonstrated as follows. Nanomole levels of avidin protein in solution can be detected by following the fluorescence intensity change of MPS-PPV and template polymer 3 complex. As shown in FIG. 2, the addition of nanomole of avidin protein to MPS-PPV-3 complex induced the decrease of MPS-PPV fluorescence; while in the controlled experiment of the addition of same amount of avidin to MPS-PPV-PDDA (4) complex solution resulted in no fluorescence change. The fluorescence spectra were recorded on a PTI Quantamaster Spectrofluorometer with excitation at 500 nm. The concentration of MPS-PPV was $1 \times 10^{-5}$ M, and the concentration of polymer 3 was $1.5 \times 10^{-5}$ M. The concentrations of added avidin were: a: 0 M; b: $2.5 \times 10^{-9}$ M; c: $5.0 \times 10^{-9}$ M; d: $1.2 \times 10^{-8}$ M. Inset: the fluorescence spectra of MPS-PPV-4 complex in the presence of different concentration of avidin. a': 0 M; b': $2.5 \times 10^{-9}$ M; c': $5.0 \times 10^{-9}$ M. It has also been observed that the presence of albumin protein (0.1 mg/ml) does not induce any fluorescence change.

EXAMPLE 3

Synthesis of a biotin substituted diallylamine derivative was as follows. A 50 ml round bottom flask was charged with 0.5 g of diallylamine (5 mmol) and g potassium bicarbonate (0.01 mol) in 20 ml dimethylformamide (DMF) under nitrogen. To the above solution was added N-(biotinoyl)-N'-(iodoacetyl)ethylenediamine (50 mg, 0.1 mmol in 5 ml DMF) in one portion at room temperature. The reaction was stirred for 12 hours at room temperature and a slightly yellow solution was obtained. TLC analysis showed the complete consumption of N-(biotinoyl)-N'-(iodoacetyl) ethylenediamine and the formation of product. To the resulting solution was added 1 g iodomethane and the reaction mixture was stirred for another 5 hours at room temperature. DMF was then removed by rotary evaporation, and the residue was dissolved in chloroform. The resulting organic solution was washed three times with water, once with brine, dried over anhydrous sodium sulfate and concentrated under reduced pressure. The liquid residue was then dried under the vacuum oven to yield the mixture of N-methyldiallylamine and its biotin-substituted derivative.

EXAMPLE 4

Synthesis of a diallylammonium derivative monomer (2) was as follows. To a solution of the above product in DMF (25 ml) was added iodomethane (1.5 g, 0.01 mol) in room temperature under nitrogen. The reaction was stirred for 12 hours in the dark. DMF and access of iodomethane were removed by rotary evaporation. The residue was then dissolved in DMF again and recrystallized from tetrahydrofuran to produce the mixture of diallylammonium derivative monomer.

EXAMPLE 5

Synthesis of a template polymer (3) was as follows. A solution of the mixture of diallydimethylammonium chloride (Aldrich) (1) and 2 at molar ratio of 1:2=100:1 in deionized water (10% w/w) was placed in a flask under the nitrogen. After the monomer was completely dissolved, the monomer solution was polymerized in the presence of a small amount of ammonium persulfate (0.1 g) at 60° C. The reaction was stirred for 12 hours in the dark. The obtained reaction mixtures were dialysed against water using dialysis tubes (Spectrum Laboratories, Inc, spectra/pro membrane (29 mm), cut off 3,500 Dalton) for 72 hours at room temperature to yield template polymer (3) stock solution. Pure polymer can be obtained by subsequently freezedrying. The obtained polymer 3 was characterized by $^1$H-NMR (Varian 200 MHz), in which the spectra showed the complete absence of carbon-carbon double bond bands.

Although the present invention has been described with reference to is specific details, it is not intended that such details should be regarded as limitations upon the scope of the invention, except as and to the extent that they are included in the accompanying claims.

What is claimed is:

1. A chemical moiety comprising the polymeric reaction product of (i) a polyelectrolyte monomer of poly (diallyldimethylammonium chloride) and (ii) a biological agent recognition element-substituted polyelectrolyte monomer of poly(diallyldimethylammonium chloride).

2. The chemical moiety of claim 1 wherein said biological agent recognition element is selected from the group consisting of chemical ligands, antibodies, antibody fragments, oligonucleotides, antigens, polypeptides, glycolipids, proteins, enzymes, peptide nucleic acids and polysaccharides.

3. The chemical moiety of claim 1 wherein said polymeric reaction product is of (i) monomer of poly (diallyldimethylammonium chloride) and (ii) a biotin-substituted monomer of poly(diallyldimethylammonium chloride).

4. A kit for the detection of biological agents comprising:

a fluorescent polymer; and, a chemical moiety of claim 1.

\* \* \* \* \*